(12) United States Patent
Huang et al.

(10) Patent No.: US 9,625,480 B2
(45) Date of Patent: Apr. 18, 2017

(54) LINKAGE CONTROL DEVICE AND BLOOD GAS ANALYZER ADOPTING SAME

(75) Inventors: Gaoxiang Huang, Shenzhen (CN); Zhixiang Zhao, Shenzhen (CN)

(73) Assignee: EDAN INSTRUMENTS INC, Shenzhen (CN)

(*) Notice: Subject to any disclaimer, the term of this patent is extended or adjusted under 35 U.S.C. 154(b) by 0 days.

(21) Appl. No.: 14/414,078

(22) PCT Filed: Jul. 30, 2012

(86) PCT No.: PCT/CN2012/079351
§ 371 (c)(1),
(2), (4) Date: Jan. 9, 2015

(87) PCT Pub. No.: WO2014/008688
PCT Pub. Date: Jan. 16, 2014

(65) Prior Publication Data
US 2015/0260743 A1    Sep. 17, 2015

(30) Foreign Application Priority Data
Jul. 13, 2012  (CN) .......................... 2012 1 0241945

(51) Int. Cl.
*B01L 99/00*    (2010.01)
*G05B 21/00*    (2006.01)
(Continued)

(52) U.S. Cl.
CPC ......... *G01N 35/00712* (2013.01); *F16K 1/24* (2013.01); *G01N 33/4925* (2013.01);
(Continued)

(58) Field of Classification Search
CPC . F16K 13/00; F16K 13/10; F16K 3/00; G05B 21/00; G01N 31/00; B01L 99/00
(Continued)

(56) References Cited

U.S. PATENT DOCUMENTS 5,630,986 A    5/1997  Charlton
5,848,610 A *  12/1998 Livernash et al. ....... 137/625.11
(Continued)

FOREIGN PATENT DOCUMENTS

CN    2375835 Y    4/2000
CN    2438881 Y    7/2001
(Continued)

OTHER PUBLICATIONS

International Search Report dated Mar. 22, 2013.

*Primary Examiner* — Brian J Sines
(74) *Attorney, Agent, or Firm* — Symbus Law Group, LLC; Clifford D. Hyra (57) ABSTRACT

Disclosed are a linkage control device and a blood gas analyzer adopting the linkage control device. The linkage control device comprises a power unit and a rotating component (4) provided with bosses (41, 42). The power unit generates power to drive the rotating component (4) to rotate. The linkage control device further comprises valve components (5, 6, 7, 8), a signal control unit, sensing switches, and sensing pins (43, 44, 45, 46). The valve components (5, 6, 7, 8) are matched with the bosses (41, 42) of the rotating component (4) in a pushing manner. The signal control unit controls the start or stop of the power unit. The sensing switches are connected to the signal control unit via signals. The sensing pins (43, 44, 45, 46) are arranged in pair with the sensing switches and are arranged on the rotating component (4).

6 Claims, 9 Drawing Sheets

(51) Int. Cl.
*G01N 31/00* (2006.01)
*F16K 13/00* (2006.01)
*F16K 13/10* (2006.01)
*F16K 3/00* (2006.01)
*G01N 35/00* (2006.01)
*F16K 1/24* (2006.01)
*G01N 33/49* (2006.01)
*F01L 1/04* (2006.01)

(52) U.S. Cl.
CPC ........ *G01N 35/00693* (2013.01); *F01L 1/042* (2013.01); *F01L 2105/00* (2013.01); *Y10T 436/115831* (2015.01)

(58) Field of Classification Search
USPC ....... 422/537, 538, 539, 540, 105, 107, 108, 422/113, 114, 63; 137/247, 247.13; 700/266; 702/24
See application file for complete search history.

(56) References Cited

U.S. PATENT DOCUMENTS

| | | | |
|---|---|---|---|
| 6,206,043 | B1* | 3/2001 | Griswold et al. ........ 137/625.44 |
| 2009/0027640 | A1* | 1/2009 | Shibazaki et al. .............. 355/53 |
| 2010/0230613 | A1* | 9/2010 | Pieprzyk et al. .......... 250/459.1 |
| 2011/0000233 | A1* | 1/2011 | Rybaski et al. ................... 62/66 |
| 2012/0193558 | A1* | 8/2012 | Hoots et al. .................... 251/89 |

FOREIGN PATENT DOCUMENTS

| | | |
|---|---|---|
| CN | 101029898 A | 9/2007 |
| CN | 201382946 Y | 1/2010 |
| CN | 201594476 U | 9/2010 |
| CN | 102419375 A | 4/2012 |

* cited by examiner

LINKAGE CONTROL DEVICE AND BLOOD GAS ANALYZER ADOPTING SAME

This application claims the benefit of Chinese patent application No. 201210241945.3, filed Jul. 13, 2012, which is hereby incorporated by reference in its entirety.

FIELD OF THE INVENTION

The invention relates to the field of medical apparatus, in particular to a linkage control device in the field of medical apparatus; the invention also relates to a blood gas analyzer.

BACKGROUND

Switch control structures are widely used in machinery and equipment; the current switch control mode on the market mainly relies on electromagnetic force switches or mechanical switches to achieve the on-off control of liquid circuits, gas circuits and electric circuits, etc. The direct point-to-point control mode can realize effective and short-time control of switches to be controlled. For example, machine power switches or pipe valve switches and so on can use mechanical switches to realize manual control or use electromagnetic switches to achieve automatic control of electric circuits.

Mechanical switches in sophisticated equipment are unable to achieve linkage control of each switch by manual operation, and if solenoid valves are used to control each switch, for one thing, there are too many valves, signal input channels and signal output channels arranged on a control panel and used for controlling valves correspondingly increase so that the linkage effect among switches becomes unreliable; for another, too many solenoid valves increase the cost of switch elements and the cost of circuit control. Therefore, in case of higher requirements for linkage, several above-mentioned switch control structures are unable to provide a stable linkage guarantee in addition to relatively high cost.

A document (Publication Number: CN 201594476 U) discloses a new-type cam switch, comprising a switch base, a cam, slide bars and electrical contact springs; the cam, comprising an upper cam and a lower cam, is arranged on the switch base via a camshaft; the eccentric angle difference between the upper cam and the lower cam is 15-45 degrees, both sides of the cam are provided with slide bars which are in active link to the switch base, up-down staggered and in touch with the cam via tops; the electrical contact springs are classified into static contact springs and movable contact springs, the slide bars are provided with movable contact springs, static contact springs are arranged on the switch base corresponding to movable contact springs, and a return mechanism is arranged between the slide bars and the switch base. The new-type cam switch is simple in structure, and both the slide bars are flexible in motion. However, the new-type cam switch cannot be used for more switch control structures, in particular to precise medical equipment with many switches, and is unable to conduct accurate linkage control of switches.

With the development of technology, control of switches in precise medical equipment is increasingly demanding. For example, medical equipment (such as blood gas analyzers, blood analyzers and biochemical analyzers, etc.) has linkage control of liquid circuits, gas circuits and electric circuits, etc. Under the circumstances, the switch control sequence linkage shall be more precise; in addition, the cost of switches shall be subject to strict control as more switches are in use.

DISCLOSURE

In order to overcome the above-mentioned disadvantages, to achieve the best control effect, to conduct precise control of the time sequence of a variety of liquid and gas switches, and to minimize the cost without disorder caused by mutual effect, a linkage control device, capable of providing stable and accurate linkage control with lower cost and simpler structure, is provided.

A blood gas analyzer to which the linkage control device is applied is also provided.

A linkage control device comprises a rack and following devices arranged thereof: a power unit, a rotating component provided with bosses and driven by the power unit, and a valve component matched with the bosses of the rotating component in a pushing manner; also comprising a signal control unit for controlling the startup or poweroff of the power unit, sensing switches connected to the signal control unit via signals, and sensing pins arranged in pair with the sensing switches and placed on the rotating component.

Further, the linkage control device comprises a gearbox, which is respectively in transmission connection to the power unit and the rotating component.

Further, the valve component comprises a valve main body and a pressure spring, the pressure spring is sleeved on the valve main body, and both ends of the pressure spring are respectively positioned on the valve main body and the main frame.

Further, the valve component also comprises a roller wheel, which is connected to the valve main body via an iron shaft pin.

Further, the number of the roller wheel can be one or two.

Further, the sensing switches are optocoupler sensing switches.

Further, the rotating component can be provided with one or more bosses.

Further, the rotating component provided with bosses is a cam.

A blood gas analyzer comprises a main frame and following devices arranged thereof: a test card, reagent packs and a vacuum pump; and also comprises a linkage control device arranged on the main frame. The valve component comprises a calibration fluid valve, an air valve, a sample valve and a current valve. The signal control unit is integrated in the control circuit of the blood gas analyzer.

A control method applied to the blood gas analyzer, wherein the signal control unit starts the power unit to run after detecting a sample inserted; when the calibration liquid sensing pin triggers the sensing switches and transmits the signal to the signal control unit, the signal control unit controls the power unit to shut down, the vacuum pump extracts calibration liquid, and the signal control unit starts the power unit to run after detecting a specified amount of calibration liquid is extracted; the air sensing pin triggers the sensing switches and transmits the signal to the signal control unit, the signal control unit controls the power unit to shut down, the vacuum pump extracts air, and the signal control unit starts the power unit to run after detecting a specified amount of air is extracted; the sample sensing pin triggers the sensing switches and transmits the signal to the signal control unit, the signal control unit controls the power unit to shut down, the vacuum pump extracts samples, the machine starts sample detection after the signal control unit detects a specified amount of sample is extracted, after the detection the signal control unit starts the power unit to run.

The invention provides in embodiments a linkage control device and a blood gas analyzer adopting same to conduct precise control of the time sequence of a variety of liquid and gas switches, to minimize the cost without disorder caused by mutual effect, and to achieve the best control effect. It is simple in structure, lower in cost and stable and accurate in linkage control.

BRIEF DESCRIPTION OF THE DRAWINGS

For a clear description, a detailed description is made by the following embodiments and attached drawings.

DETAILED DESCRIPTION OF EMBODIMENTS

In order to make the objective, the technical scheme and advantages of the invention clearer, further detailed description of the invention is made as below in combination with the accompanying drawings and embodiments. It shall be understood that, these embodiments are only used for explaining instead of limiting the invention.

Figure 1:
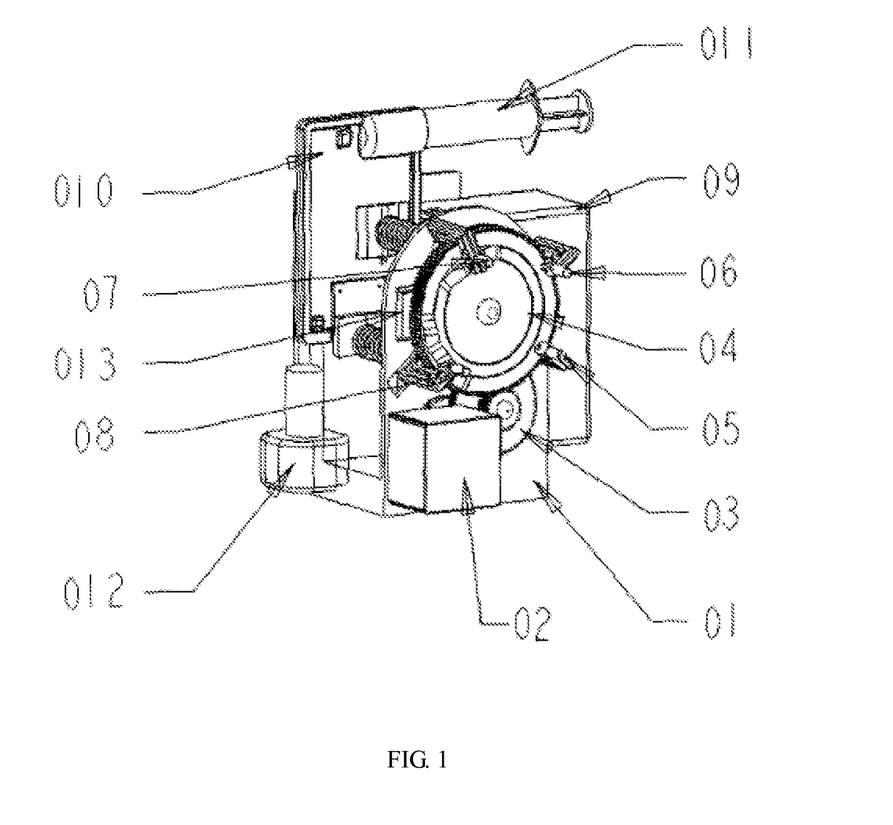
FIG. 1 is an overall schematic diagram of the blood gas analyzer using the linkage control device in an embodiment of the invention.

Further detailed description of the invention is made by taking the blood gas analyzer as an example (as shown in FIG. 1).

The blood gas analyzer includes: a valve control device, a reagent pack device, a test card, a vacuum pump and a main frame; the valve control device, the reagent pack device and the vacuum pump are arranged on the main frame; the cam linkage structure is arranged on the main frame; the test card and the reagent pack are inserted between the bracket and the valve components; and the test card and the reagent pack device are connected with the vacuum pump.

A linkage control device applied to a blood gas analyzer includes: a bracket and following devices arranged thereof: a motor power unit, a control circuit, a gearbox, a cam, four valve components, a test card component, a reagent pack component and a vacuum pump component; the motor power unit, the gearbox and the cam are arranged on one side of the bracket; the reagent pack component, the test card component and the vacuum pump component are arranged on the other side of the bracket via the base; four valves (the calibration liquid valve, the air valve, the sample valve and the current valve) are arranged on the bracket between the cam and the test card and rely on the cam for control.

Structures of components of the blood gas analyzer (as shown in FIGS. 2-12).

Figure 2:
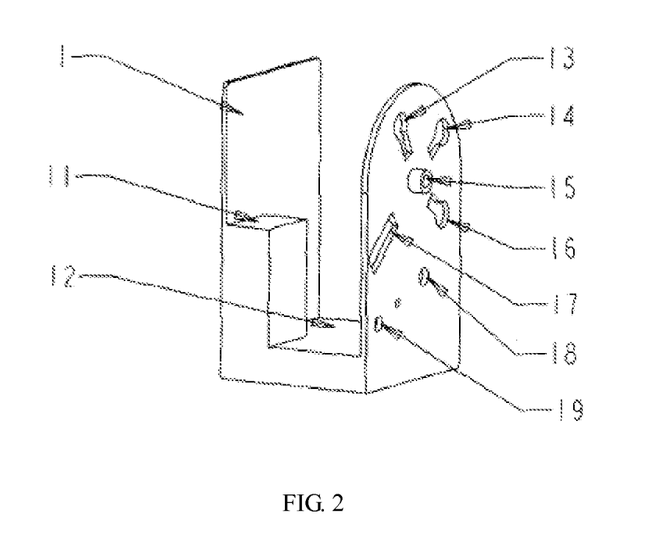
FIG. 2 is a schematic diagram of the bracket of the blood gas analyzer using the linkage control device in an embodiment of the invention.

The bracket 01 is a U-shaped structure; the same bracket is provided a test card base 11, a reagent pack base 12, a motor assembly hole 19, a gearbox assembly hole 18, a cam assembly hole 15, a calibration liquid valve assembly hole 16, an air valve assembly hole 14, a sample valve assembly hole 13 and a current valve assembly hole 17 for assembling the above-mentioned components.

Figure 3:
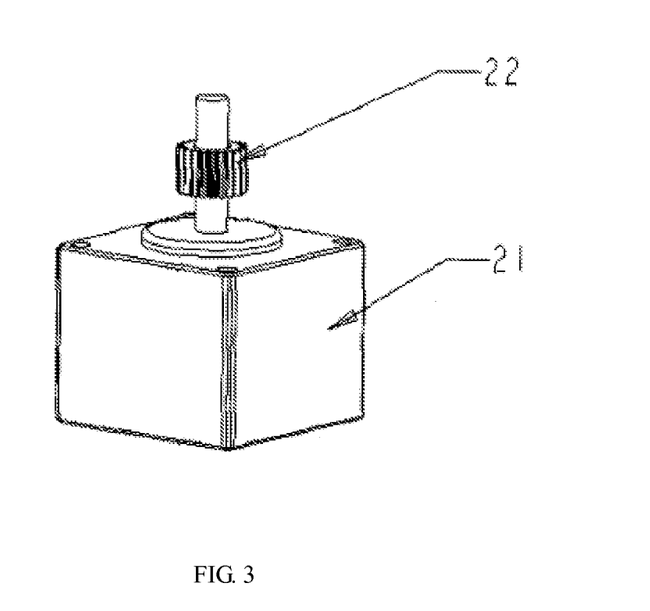
FIG. 3 is a schematic diagram of the motor power unit of the blood gas analyzer using the linkage control device in an embodiment of the invention.

A motor power unit 02 comprises a motor 21 and gears 22 fixed to the motor; when the motor 21 is running, it drives the gears 22 to rotate, and thus providing source of power for the gearbox.

Figure 4:
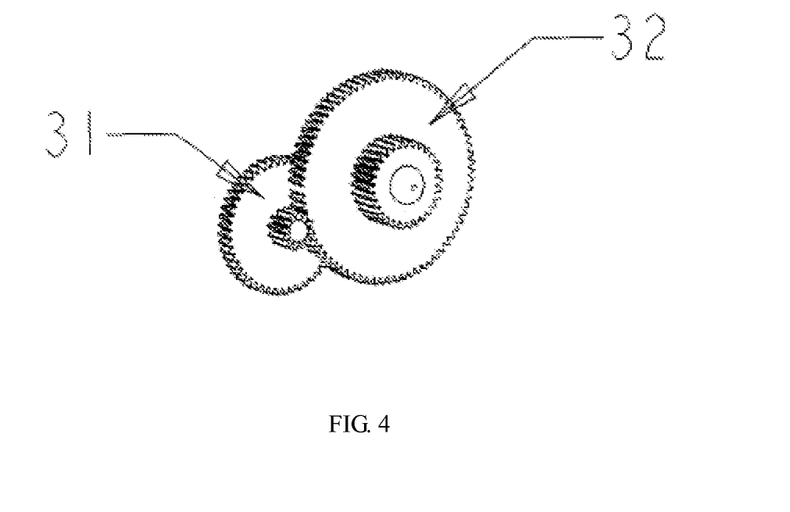
FIG. 4 is a schematic diagram of the gearbox component of the blood gas analyzer using the linkage control device in an embodiment of the invention.

A gearbox component 03 comprises two variable gears (a variable gear 31 and a variable gear 32) assembled on the bracket 01. The variable gears play a role in reducing speed.

Figure 5:
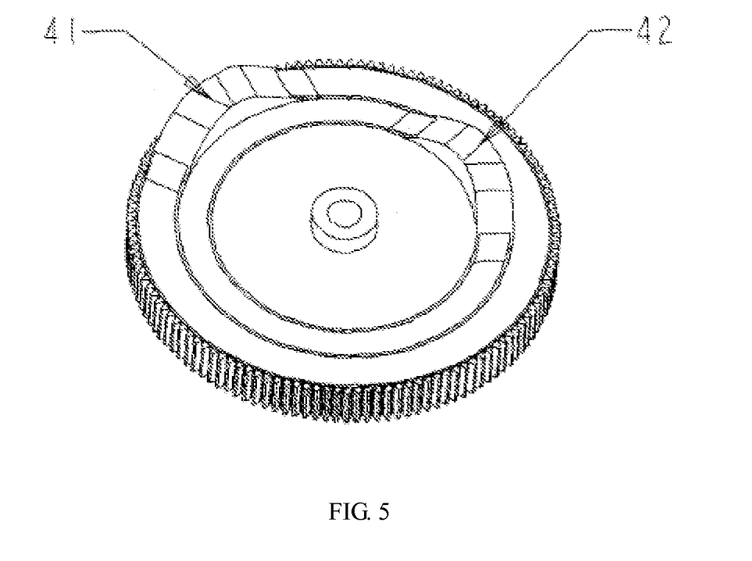
FIG. 5 is a schematic diagram of the bosses on the front side of the cam of the blood gas analyzer using the linkage control device in an embodiment of the invention.
Figure 6:
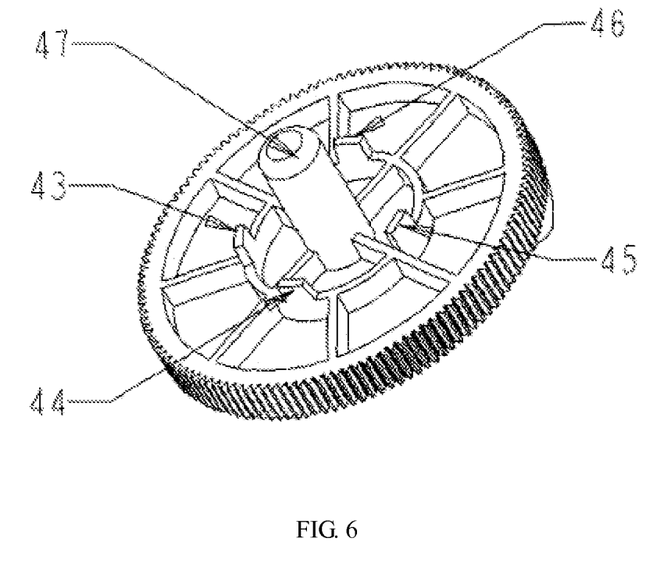
FIG. 6 is a schematic diagram of the optocoupler switch sensing pins on the reverse side of the cam of the blood gas analyzer using the linkage control device in an embodiment of the invention.

A cam 04 comprises peripheral cams provided with gears; the front side of the cam is provided with a smooth bulge (must be a smooth bulge instead of a ladder bulge, otherwise it is impossible to realize on-off of valves) whose both sides have gradient; two bosses of the smooth bulge are a first boss 41 and a second boss 42 respectively for on-off control of valves; both the first boss 41 and the second boss 42 are respectively arranged on different radiuses of the cam for respective control of valves; four sensing pins arranged on the reverse side of the cam respectively are: a calibration liquid sensing pin 43, an air sensing pin 44, a sample sensing pin 45 and a current sensing pin 46 respectively used for position detection of valves, here optical couplers are preferred because signal from optical couplers are in unidirectional transmission, both the input terminal and the output terminal completely realize electric isolation, and output signal has no influence on the input terminal, thus ensuring the linkage effect more stable. The cam is provided with an assembly column 47 assembled on the cam assembly hole 15 of the bracket 01.

Figure 7:
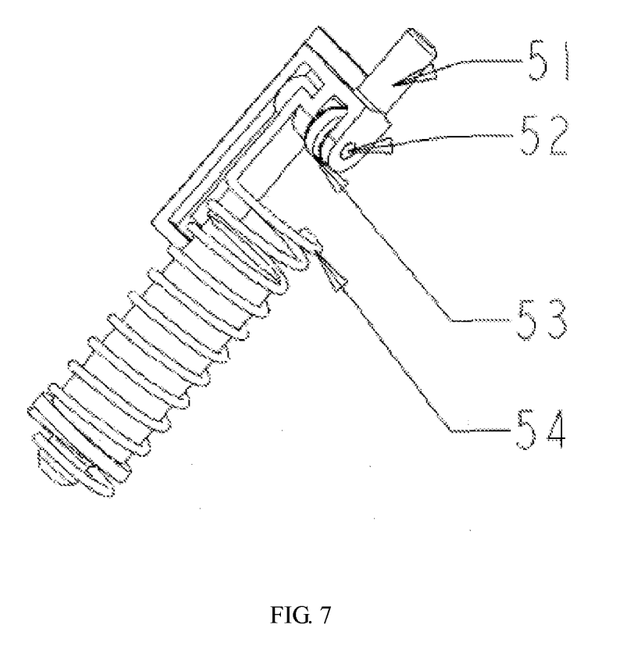
FIG. 7 is a schematic diagram of the calibration liquid valve component of the blood gas analyzer using the linkage control device in an embodiment of the invention.

A calibration liquid valve component 05 comprises a valve main body 51, a roller wheel 53 is assembled by an iron shaft 52 on the contact position between the valve and the cam for contacting the cam surface and rolling on the cam so as to reduce friction force; also a pressure spring 54 is assembled on the valve main body, and the whole calibration liquid valve component is arranged between the bracket 1 and the cam 4.

Figure 8:
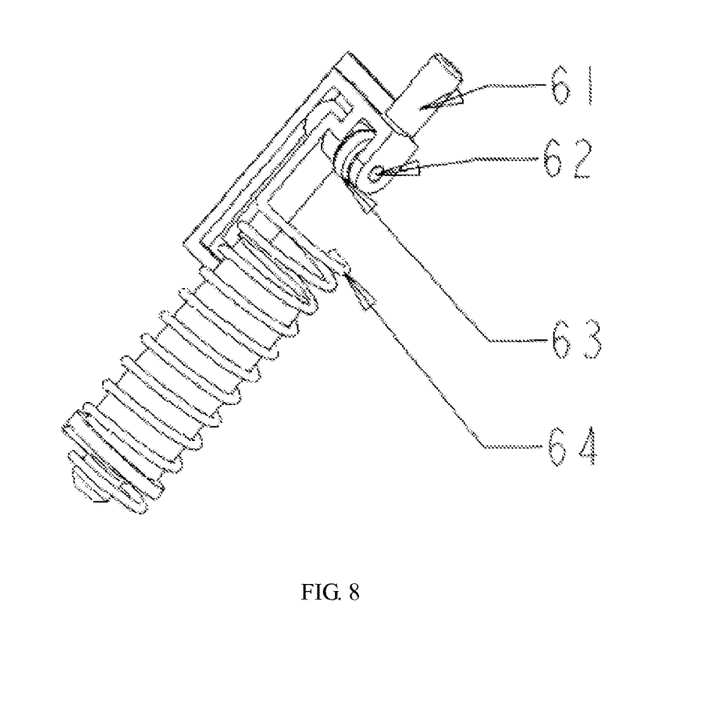
FIG. 8 is a schematic diagram of the air valve component of the blood gas analyzer using the linkage control device in an embodiment of the invention.

An air valve component 06 comprises a valve main body 61, a roller wheel 63 is assembled by an iron shaft 62 on the contact position between the valve and the cam for contacting the cam surface and rolling on the cam so as to reduce friction force; also a pressure spring 64 is assembled on the valve main body, and the whole calibration liquid valve component is arranged between the bracket 1 and the cam 4.

Figure 9:
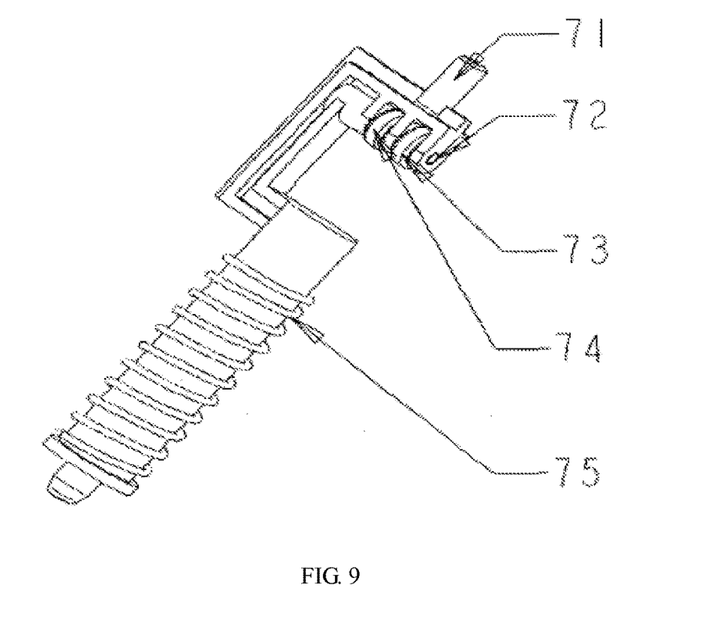
FIG. 9 is a schematic diagram of the sample valve component of the blood gas analyzer using the linkage control device in an embodiment of the invention.

A sample valve component 07 comprises a valve main body 71, two roller wheels (a first roller wheel 73 and a second roller wheel 74) are assembled by an iron shaft 72 on the contact position between the valve and the cam for contacting the cam surface and rolling on the cam so as to reduce friction force, and under the control of the first boss 41 and the second boss 42 on the cam; also a pressure spring 75 is assembled on the valve main body, and the whole calibration liquid valve component is arranged between the bracket 1 and the cam 4.

Figure 10:
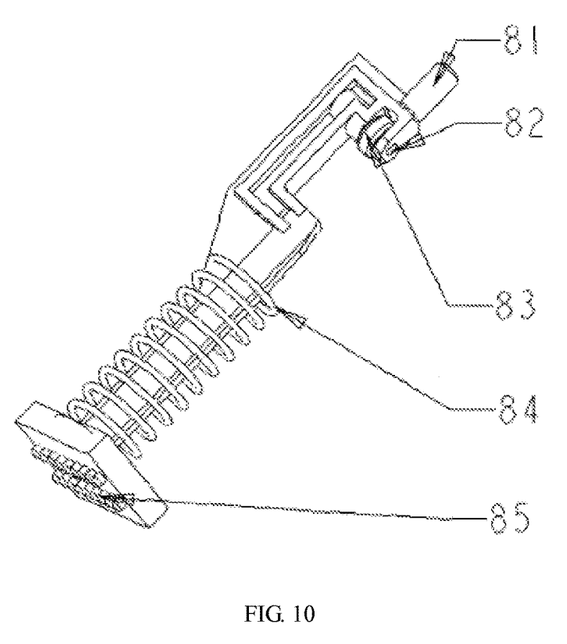
FIG. 10 is a schematic diagram of the current valve component of the blood gas analyzer using the linkage control device in an embodiment of the invention.

A current valve component 08 comprises a valve main body 81, a roller wheel 83 is assembled by an iron shaft 82 on the contact position between the valve and the cam for contacting the cam surface and rolling on the cam so as to reduce friction force; also a pressure spring 84 is assembled on the valve main body, and the other end of the valve main body is provided with a group of conductive contacts 85. The whole calibration liquid valve component is arranged between the bracket 1 and the cam 4.

Figure 11:
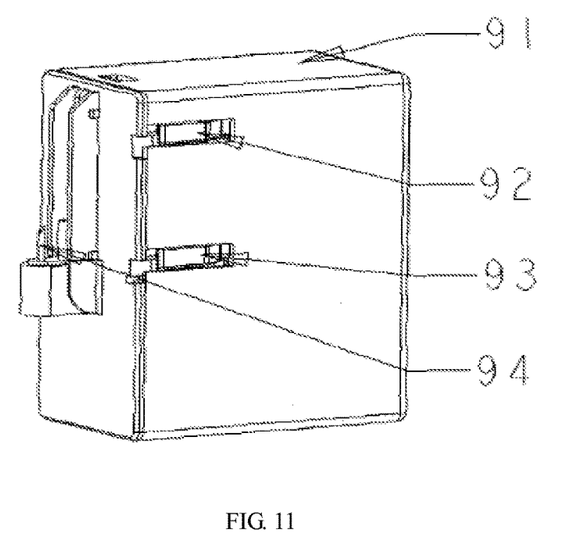
FIG. 11 is a schematic diagram of the reagent pack component of the blood gas analyzer using the linkage control device in an embodiment of the invention.

A reagent pack component 09 comprises a pack body 91 for providing calibration liquid, an air delivery control valve 92, and a calibration liquid delivery control valve 93; one side of the reagent pack body 91 is provided with a steel needle 94 for inserting into the test card component 10 so as to communicate to the reagent pack and the test card.

Figure 12:
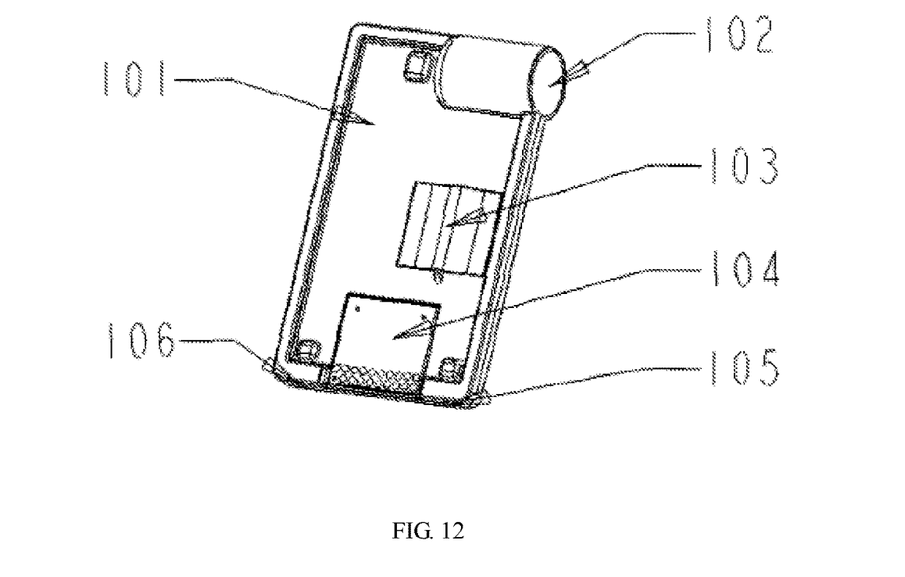
FIG. 12 is a schematic diagram of the test card component of the blood gas analyzer using the linkage control device in an embodiment of the invention.

The test card component 10 comprises a test card main body 101, an injector inlet 102 for providing sample, a sample valve 103, a current board 104, a reagent pack inlet 105 and a vacuum pump inlet 106.

Description of characteristics and assembly methods of structural members is as below:

The motor power unit 02 is assembled on the U-shaped bracket 01 through the motor assembly hole 19; the first variable gear 31 and the second variable gear 32 are assembled on the U-shaped bracket 01 through the gearbox assembly hole 18; the cam is assembled on the U-shaped bracket 01 through the cam assembly hole 16; likewise, the calibration liquid valve component 05, the air valve component 06, the sample valve component 07 and the current valve component 08 are successively assembled on the U-shaped bracket 01 through the calibration liquid valve assembly hole 16, the air valve assembly hole 14, the sample valve assembly hole 13 and the current valve assembly hole 17; the test card component 10 is assembled inside the U-shaped bracket via the test card base 11; and the reagent pack component 9 is assembled via the reagent pack base 12.

In the on-off control process of valves, control of a plurality of valves can be achieved by interval rotation of the cam as long as control circuit signal is input so that motors are controlled by the control circuit, while the control circuit signal can be obtained by triggering induction when the cam is rotated to corresponding position, thus forming an ordered linkage control mechanism.

Detailed control process:

1. The initial state (see FIGS. 1 and 13): the calibration liquid valve component 05 and the air valve component 06, under the action of respective valve pressure spring force, press the calibration liquid delivery control valve 93 and the air delivery control valve 92 on the reagent pack component 09 so that both the calibration liquid delivery control valve 93 and the air delivery control valve 92 are at off state; the first boss 41 on the cam 04 props the current valve roller wheel 83 and switches on the current valve component 08, the second boss 42 props the first roller wheel 73 of the sample valve and switches on the sample valve component 07; both valves are released so that valves maintain the on state while current maintains the off state for the convenience of insertion and extraction of the test card component 010.

Figure 13:
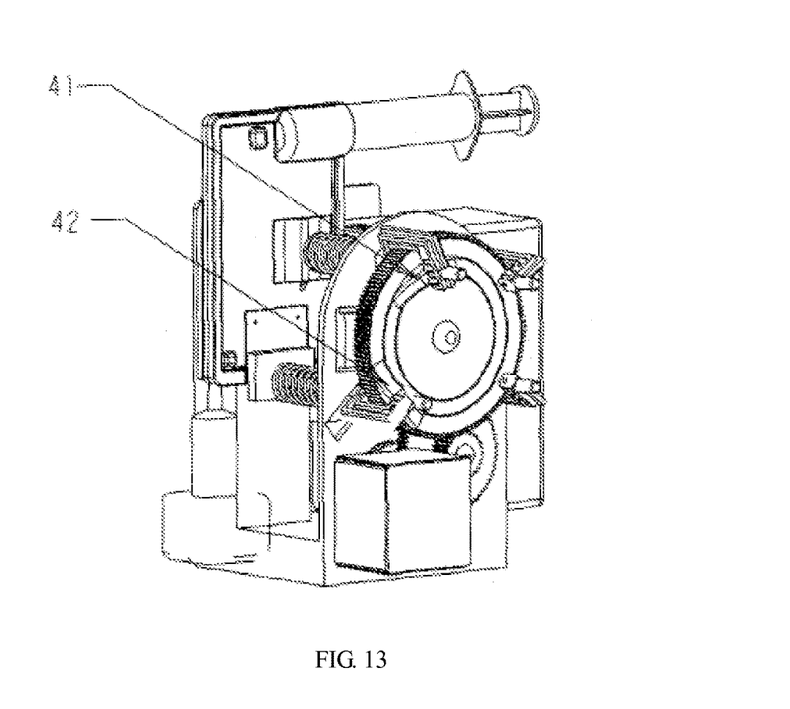
FIG. 13 is a schematic diagram of the initial working state of the blood gas analyzer using the linkage control device in an embodiment of the invention.

2. Startup state: after the test card component 010 is inserted, the injector 011 with a sample is also inserted into the injector inlet 102 on the test card component; the control circuit system starts the motor power unit 02 to run after detecting that the sample has been inserted, and drives the cam 04 to rotate via the gearbox 03; the first boss 41 and the second boss 42 on the cam 04 simultaneously release the current valve roller wheel 83 and the first roller wheel of the sample valve, and switch off the sample valve component 07 and the current valve component 08, in this way, under the action of the pressure spring 75, the sample valve presses the sample valve 103 on the test card so that the sample is at the off state. In addition, under the action of the pressure spring 84, the current valve component 08 ensures the conductive contacts 85 at the front end of the current valve to press the current board 104 on the test card component so that test current is at the on state.

Figure 14:
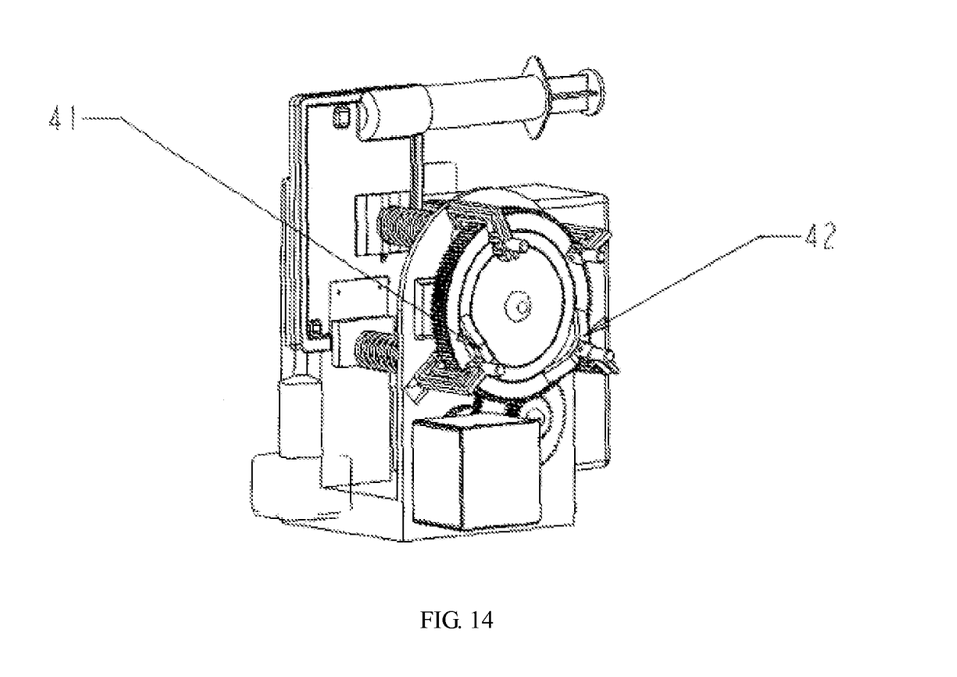
FIG. 14 is a schematic diagram of the calibration liquid extraction working state of the blood gas analyzer using the linkage control device in an embodiment of the invention.

3. Calibration liquid extraction state (see FIGS. 1 and 14): the motor power unit 02 continues running, and drives the cam 04 to rotate via the gearbox 03; when the calibration liquid valve roller wheel 53 on the calibration liquid valve component 05 is switched on by the first boss 41 on the cam 04, the calibration liquid delivery control valve 93 on the reagent pack component 09 is released by the calibration liquid valve component 05, thus keeping the channel of calibration liquid open; at this moment, the calibration liquid sensing pin 43 on the cam 04 triggers the optocoupler sensing switch 013, thus shutting down the motor power unit 02. The vacuum pump component 012 starts to run for extraction of calibration liquid.

Figure 15:
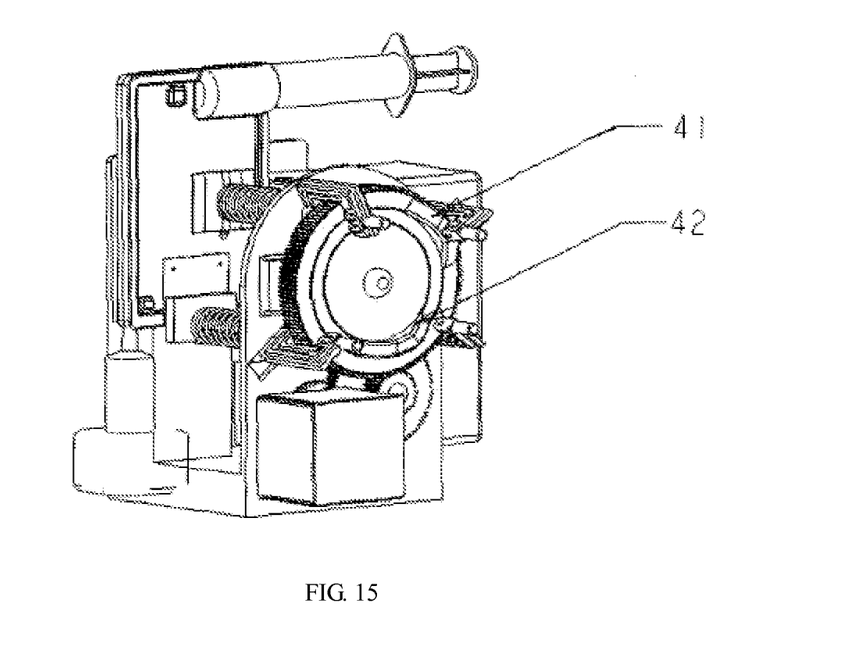
FIG. 15 is a schematic diagram of the air extraction working state of the blood gas analyzer using the linkage control device in an embodiment of the invention.

4. Air extraction state (see FIGS. 1 and 15): when the control circuit detects that a specified amount of calibration liquid is extracted, the control circuit gives a signal for triggering the motor power unit 02 to run, the calibration liquid valve roller wheel 53 is firstly released by the first boss 41 on the cam 04 so as to switch off the calibration liquid valve component 05; under the action of the calibration liquid valve pressure spring 54, the calibration liquid valve component 05 re-presses the calibration liquid delivery control valve 93 on the reagent pack component 09 so as to close the calibration liquid channel; when the first boss 41 on the cam 04 rotates to open the air valve roller wheel 63 and opens the air valve component 06, the air delivery control valve 92 on the reagent pack component 09 is released, thus keeping the air channel open; at this moment, the air sensing pin 44 on the cam 04 triggers the optocoupler sensing switch 013, thus shutting down the motor power unit 02. At this moment, the vacuum pump component 012 starts to run for extraction of air.

Figure 16:
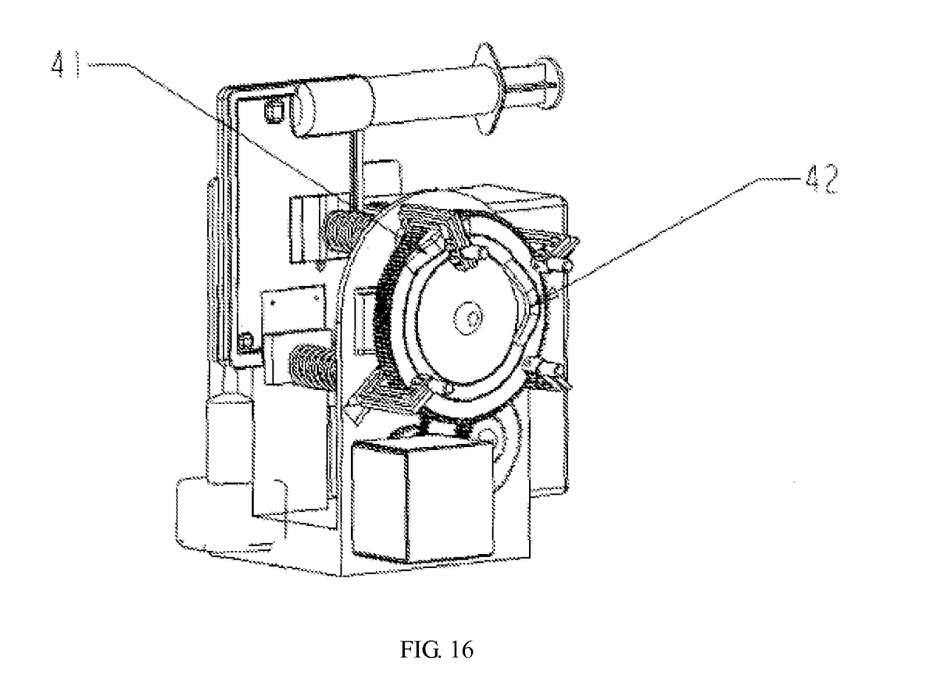
FIG. 16 is a schematic diagram of the sample extraction working state of the blood gas analyzer using the linkage control device in an embodiment of the invention.

5. Sample extraction state (see FIGS. 1 and 16): when a specified amount of air is extracted, the motor power unit 02 is triggered to run, the air valve roller wheel 63 is firstly released by the first boss 41 on the cam 04 so as to switch off the air valve component 06; under the action of the air valve pressure spring 64, the air valve component 06 re-presses the air delivery control valve 92 on the reagent pack component 09 so as to close the air channel; when the first boss 41 on the cam 04 rotates to open the second roller wheel 74 on the sample valve and opens the sample valve component 07, the sample delivery valve 103 on the test card component 010 is released, thus keeping the air channel open; at this moment, the air sensing pin 45 on the cam 04 triggers the optocoupler sensing switch 013, thus shutting down the motor power unit 02. At this moment, the vacuum pump component 012 starts to run for extraction of sample.

6. Returning to the initial state after sample detection: the machine starts sample detection when a specified amount of sample is extracted. After the control circuit detects that sample detection is completed, the control circuit gives a signal for triggering the motor power unit 02 to run, the second roller wheel 74 of the sample valve is firstly released by the first boss 41 on the cam 04 so as to switch off the sample valve component 07; under the action of the sample valve pressure spring 75, the sample valve component 07 re-presses the sample delivery valve 103 on the test card component 010 so as to close the sample delivery valve channel; at this moment, the motor power unit 02 continues running, the current valve component 08 is switched on when the first boss 41 on the cam 04 rotates and opens the roller wheel 83 of the current valve so that the conductive contacts 85 at the front end of the current valve component 08 get away from the current board 104 on the test card component, thus ensuring test current at the off state; in addition, the sample valve component 07 is switched on when the second boss 42 on the cam 04 rotates and opens the first roller wheel 73 of the sample valve, the sample delivery valve 103 on the test card component 010 is released so as to keep the air channel open, for the convenience of insertion and extraction of the test card component 010. In this way, the test card component 010 can be smoothly extracted. Also, it is convenient for insertion of the next test card component for the next test.

The blood gas analyzer includes calibration liquid for calibrating test card and human blood for test; both liquids and a kind of gas flow through the test card for calibration and test; in order to obtain the best test results, the time sequence of liquid and gas switches shall be subject to accurate control during test, without disorder caused by interaction effect; besides, the cost shall be minimized. Both the entry time sequence and the usage amount of calibration liquid, gas and sample shall be subject to strict control, which can be achieved by adjusting the effective length of the bulge and the position of bosses on the cam.

The linkage control device can also be used for control of separate liquid circuits, gas circuits and electric circuits, etc. Besides, more complex control can be realized by arranging a plurality of cams or arranging one or more bosses on one cam.

The above-mentioned embodiments are merely embodiments of the invention, not for limiting the invention. Any modification, equivalent substitution and improvement in the spirit and principle of the invention are within the scope of protection of the invention.

The invention claimed is:

1. A linkage control device comprises
    a rack and following devices arranged thereof:
        a power unit,
        a rotating component provided with at least one boss and driven by the power unit, and
        a valve component matched with the bosses of the rotating component in a pushing manner, the valve component being arranged between the rack and the rotating component;
    wherein the linkage control device also comprises a signal control unit for controlling the start or stop of the power unit, sensing switches connected to the signal control unit via signals, and sensing pins arranged in pair with the sensing switches and placed on the rotating component.

2. The linkage control device according to claim 1, wherein the linkage control device also comprises a gearbox, which is respectively in transmission connection to the power unit and the rotating component.

3. The linkage control device according to claim 2, wherein the valve component comprises a valve main body and a pressure spring, the pressure spring is sleeved on the valve main body, and both ends of the pressure spring are respectively positioned on the valve main body and the main frame.

4. The linkage control device according to claim 3, wherein the valve component also comprises at least one roller wheel, which is connected to the valve main body via an iron shaft pin.

5. The linkage control device according to claim 4, wherein the sensing switches are optocoupler sensing switches.

6. The linkage control device according to claim 5, wherein the rotating component provided with at least one boss is a cam.

* * * * *